(12) United States Patent
Newhauser et al.

(10) Patent No.: US 8,241,318 B2
(45) Date of Patent: Aug. 14, 2012

(54) EMBOLIC PROTECTION DEVICE WITH LOCKING DEVICE

(75) Inventors: Richard Newhauser, San Francisco, CA (US); Travis Richard Yribarren, San Mateo, CA (US)

(73) Assignee: Abbott Laboratories, Abbott Park, IL (US)

( * ) Notice: Subject to any disclaimer, the term of this patent is extended or adjusted under 35 U.S.C. 154(b) by 960 days.

(21) Appl. No.: 11/735,052

(22) Filed: Apr. 13, 2007

(65) Prior Publication Data

US 2008/0255604 A1  Oct. 16, 2008

(51) Int. Cl.
*A61M 29/00* (2006.01)
(52) U.S. Cl. ..................................... 606/200
(58) Field of Classification Search ............... 600/434, 600/585; 606/200
See application file for complete search history.

(56) References Cited

U.S. PATENT DOCUMENTS

| | | | |
|---|---|---|---|
| 5,216,831 A * | 6/1993 | Halterman, Jr. | 43/44.91 |
| 5,769,858 A * | 6/1998 | Pearson et al. | 606/108 |
| 6,949,104 B2 * | 9/2005 | Griffis et al. | 606/108 |
| 2002/0049467 A1 * | 4/2002 | Gilson et al. | 606/200 |
| 2004/0102789 A1 * | 5/2004 | Baughman | 606/99 |
| 2004/0167566 A1 * | 8/2004 | Beulke et al. | 606/200 |
| 2004/0199198 A1 * | 10/2004 | Beulke et al. | 606/200 |
| 2006/0015139 A1 * | 1/2006 | Tsugita et al. | 606/200 |
| 2008/0045999 A1 * | 2/2008 | Tsugita et al. | 606/200 |
| 2009/0105746 A1 * | 4/2009 | Spenser et al. | 606/200 |

* cited by examiner

*Primary Examiner* — Thomas J Sweet
*Assistant Examiner* — Eric Blatt
(74) *Attorney, Agent, or Firm* — Sughrue Mion, PLLC; Jonathan D. Feuchtwang

(57) ABSTRACT

A device and method for locking onto a guidewire. The device includes an element transversely movable along the guidewire. The element may have a plurality of portions and a biasing member connecting first and second portions of the transversely moveable element such that the first portion and another of the portions are movable from a first position, where the first portion and the other portion are aligned with respect to one another, to a second position, where the first portion is no longer aligned with respect to the other portion, the device being locked to the guidewire in the second position. The device can be used for locking an embolic protection device including a filter to a guidewire that is adapted to be introduced into a vascular system of a patient.

26 Claims, 12 Drawing Sheets

EMBOLIC PROTECTION DEVICE WITH LOCKING DEVICE

BACKGROUND OF THE INVENTION

1. Field of the Invention

This invention generally relates to an embolic protection device and, more particularly, to an embolic protection device with a locking device for releasably locking the embolic protection device onto a guidewire.

2. Description of the Related Art

An embolic protection device includes a filter that captures embolic material released during an interventional procedure for treating stenosis of a patient's blood vessel. Such an embolic protection device is described in U.S. Patent Publication Nos. 2002/0049467 A1, 2002/0026213 A1, 2002/0002384 A1, and 2003/0032977 A1. The entire disclosures of these publications are incorporated herein by reference.

In an embolic protection device, a filter is deployed at a location within the patient's blood vessel which allows it to capture released embolic material. After a stenosis has been treated, the filter is retracted. For example, the embolic filter may abut a stop provided at a distal end of a guidewire. The filter may be pressed against the stop either: by advancing the filter toward the stop using a retrieval catheter, or by retracting the guidewire until the stop abuts the filter. When the filter and stop on the guidewire abut, the stop maintains the position of the filter against the force of the advancing retrieval catheter, thereby allowing the retrieval catheter to move over and collapse the filter. The collapsed filter can then be retracted from the blood vessel.

It would be beneficial to provide an embolic filter that can be used with any guidewire and, in particular, a guidewire that does not have a stop for abutting against the filter, i.e., a so-called "barewire."

BRIEF SUMMARY OF THE INVENTION

A first aspect of the invention is a device for locking a medical device onto a guidewire. The device includes an element transversely movable along the guidewire, the element having a plurality of portions. The device also includes a biasing member connecting first and second portions of the transversely moveable element. The first portion and another portion of the transversely are movable from a first position, where the first portion and the other portion are aligned with respect to one another, to a second position, where the first portion is cinched, or not aligned with respect to the other portion, and the device is locked to the guidewire.

The first portion may be moved out of alignment with respect to the second portion by, for example, being oriented at an angle with respect to the second portion or being laterally offset with respect to the other portion.

The device may be biased to move from the first position to the second position at a portion of the guidewire having a stiffness less than a predetermined biasing force of the biasing element. This may correspond to a floppy end portion of the guidewire.

One or more of the portions of the transversely moveable element may be cylindrically shaped, and the biasing member may be an elastic member that biases the first and second portions. The elastic member may be one or more elastic elements connecting the first and second portions of the transversely moveable element. For example, the elastic member can be two elastic elements that are aligned with the guidewire in the first position, each elastic element being attached at a first end to the first portion of the transversely moveable element and at a second end to the second portion of the transversely moveable element.

The first and second portions of the transversely moveable element may abut one another with the first portion and/or the second portion having an end shaped to facilitate movement of the first and second portions from the first position to the second position. Specifically, one of the first or second portions may have an end in contact with the other portion that is shaped to provide for limited contact between the first and second portions or a point, or substantially a point, contact between the first and second portions.

The first portion may also include two opposing tabs, each tab provided at an end of the first portion that is adjacent to the second portion and at a position substantially 90 degrees with respect to the elastic element.

Alternatively, the biasing member may be a helical elastic element that is connected between the first and second portions. The first portion can include an inclined proximal end, and the second portion can include an inclined distal end, the inclined proximal end of the first portion being adjacent to the inclined distal end of the second portion.

Each portion of the transversely moveable member may have at least one inclined end, and the portions of may, together, form a substantially cylindrical shape when in the first, aligned position.

In a second aspect of the invention, there is provided an embolic protection device, including a filter and the device for locking a medical device onto a guidewire described above.

Preferably, the filter can include a collapsible filter body adapted for delivery through the vascular system of the patient; the filter body being moveable between a collapsed position, which is capable of movement through the vascular system, and an expanded position, wherein the filter is capable of capturing embolic material while allowing blood to pass through the filter body. The filter body can include an inlet end and an outlet end; the inlet end having inlet openings sized to allow the blood and the embolic material to enter the filter body, and the outlet end having numerous outlet openings sized to allow passage of the blood but to retain the embolic material within the filter body.

In a third aspect of the invention, a method is provided for locking a medical device onto a guidewire. The method includes the steps of advancing a locking device along a relatively stiff portion of the guidewire, wherein first and second portions of an element that is transversely moveable along the guidewire are substantially aligned and are connected by a biasing member; providing the device at a less stiff, or floppy, portion of the guidewire; and biasing either the first portion or the second portion so that one portion of the transversely moveable element is not aligned with respect to the other portion, thereby locking the device on the guidewire.

The one portion of the transversely moveable element may be moved out of alignment by, for example, being oriented at an angle with respect to the second portion or being laterally offset with respect to the other portion.

The method may also include the steps of advancing a retracting device over the locking device so that the first and second portions of the device are again aligned with respect to one another, and retracting the device along the guidewire.

In a fourth aspect of the invention, there is provided a device for locking onto a guidewire, including an element transversely movable along a guidewire, the element comprising a collet portion, the collet portion having a deflectable tooth feature, wherein the tooth feature can be deflected from a first position to a second position, the device being locked to the guidewire in the second position.

The device may include a filter moveable on the guidewire, wherein the guidewire is adapted to be introduced into a vascular system of a patient.

In a fifth aspect of the invention, a method is provided for locking a device onto a guidewire, the guidewire including a stiff portion with a first stiffness and a floppy portion with a second, lesser stiffness. The method includes advancing the device along the stiff portion of the guidewire, the device comprising an element transversely movable along the guidewire, the element comprising a collet portion, the collet portion having at least one deflectable tooth feature, wherein the tooth feature can be deflected from a first position to a second position, the device being locked to the guidewire in the second position; providing the device at the floppy portion of the guidewire; and biasing the tooth element so that the guidewire becomes pinched between the tooth element and an opposing surface of the collet, whereby the device is locked to the guidewire.

In a sixth aspect of the invention, a device is provided for locking onto a guidewire including an element transversely movable along a guidewire, the element comprising a tubular portion, wherein the tubular portion can be deformed from a first position to a second position, the device being locked to the guidewire in the second position.

The device may include a filter moveable on the guidewire, wherein the guidewire is adapted to be introduced into a vascular system of a patient.

In a seventh aspect of the invention, a method is provided for locking a device onto a guidewire, the guidewire including a stiff portion with a first stiffness and a floppy portion with a second, lesser stiffness. The method includes advancing the device along the stiff portion of the guidewire, the device comprising an element transversely movable along the guidewire, the element comprising a tubular portion, wherein the tubular portion can be deformed from a first position to a second position, the device being locked to the guidewire in the second position; providing the device at the floppy portion of the guidewire; and deforming the tubular portion to the second position, so that a lumen of the tubular portion reduces in profile, thereby pinching the guidewire and locking the device to the guidewire.

BRIEF DESCRIPTION OF THE DRAWINGS

The nature and features of the invention will be more fully apparent upon consideration of the exemplary embodiments of the invention, which are schematically set forth in the drawings, in which.

DETAILED DESCRIPTION OF THE EXEMPLARY EMBODIMENTS

While the invention is open to various modifications and alternative forms, specific embodiments thereof are shown by way of examples in the drawings and are described herein in detail. There is no intent to limit the invention to the particular form disclosed.

Figure 1:
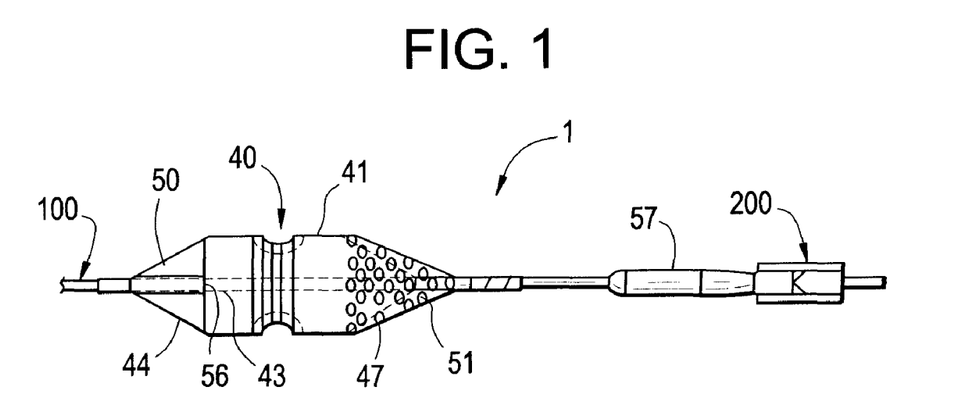
FIG. 1 is a side view of an embolic protection device according to a first exemplary embodiment of the invention.

FIG. 1 is a view of an embolic protection device 1 according to a first exemplary embodiment of the invention. The embolic protection device 1 includes a filter 40 and a guidewire lock, or brake 200. The structure of the filter 40, which is described in detail below, may include a collapsible filter body 41, a sleeve 43, and a guide olive 57. However, the invention is not limited to specific features of the filter 40.

A proximal inlet end 44 (i.e., upstream) of the filter body 41 includes one or more large inlet openings 50, and a distal outlet end 47 (i.e., downstream) of the filter body 41 includes many small outlet openings 51. The inlet openings 50 allow both blood and embolic material released during a procedure to enter the filter body 41. The outlet openings 51 allow blood to pass through the filter body 41, but the released embolic material is retained in the filter body 41.

The filter body 41 is moveable between a collapsed position (not shown), in which the filter can be delivered through a patient's vascular system and an expanded position (shown in FIG. 1), in which embolic material released during the procedure is captured within the filter body 41.

The filter 40 can also include a sleeve 43 with a lumen 56. When the filter 40 is advanced into a patient's body via a guidewire 100, the guidewire 100 is positioned within the lumen 56. The sleeve 43 prevents the released embolic material within the filter body 41 from escaping into the lumen 56.

Moreover, the guide olive 57 may be provided at a distal end 47 of the filter body 41 and can be integrally formed with the filter body 41. The guide olive 57 assists with insertion and advancement of the embolic protection device 1 into the blood vessel.

As shown in FIG. 1, the guidewire lock 200 can be provided at the distal end of the filter 40. However, the invention is not limited in this respect, and the lock 200 could also be provided at a proximal end of the filter 40.

Figure 2A:
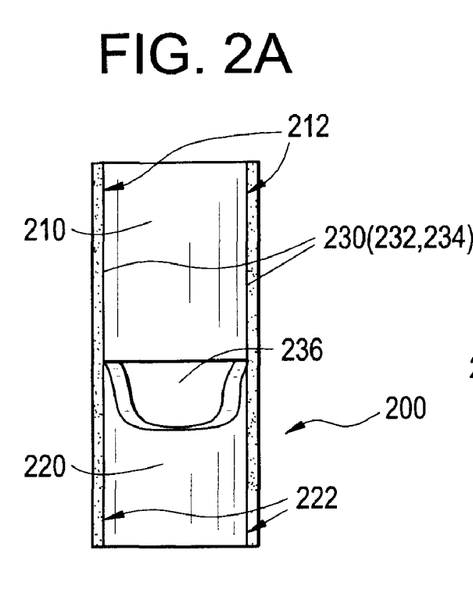
FIGS. 2A and 2B are side views of a lock according to the first exemplary embodiment of the invention.
Figure 2B:
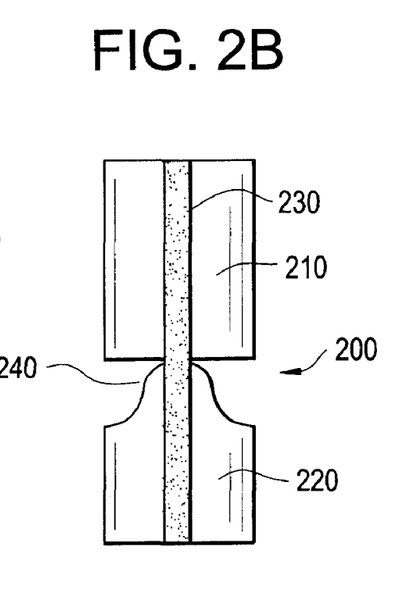

In this exemplary embodiment, the lock 200 is an element that is transversely moveable along the guidewire 100. As shown in FIGS. 2A and 2B, the lock 200 includes a transversely moveable first portion 210, a transversely moveable second portion 220, and a biasing member 230 that connects the first and second portions 210, 220. The biasing member 230 may be two elastic elements 232, 234 provided at opposing sides of the first and second portions 210, 220. Each of the elastic elements 232, 234 is attached at a first end 212 to the first portion 210 and at a second end 222 to the second portion 220.

As shown in FIGS. 2A and 2B, the first and second portions 210, 220 can abut against one another. Moreover, at least one of the first and/or the second 210, 220 portions can include openings 236 at the abutting end of the first and/or second 220 portions. These openings 236 provide a point contact 240 of decreased area, or rocking point, between the first and second portions. This rocking point decreases the stability of the first and second 210, 220 portions when they are aligned with respect to one another. As shown in FIG. 2A, the openings 236 can be snake-mouth cuts.

The first and second portions 210, 220 can be cylinders made of, for example, a biocompatible metal such as stainless steel, NITNOL, CoCr or Ti. In addition, the cylinders may be made from a hard plastic like polycarbonate, ULTEM, or acrylonitrile butadiene styrene (ABS).

The elastic elements 232, 234 can be extension springs made of, for example, NITNOL, stainless steel, or CoCr. Alternatively, the elastic elements 232, 234 could be made of a polymer with good elasticity, such as latex, silicone, polyurethane, TPE, or PEBAX.

Preferably, the first and second portions 210, 220 each have an inner diameter that is slightly larger than an outer diameter of the guidewire 100. For example, in the case of filter designed for a carotid procedure using an 0.014 inch guidewire, the inner diameter of the first and second portions 210, 220 might be about 0.0155 inches, while a wall thickness of the first and second portions 210, 220 might be 0.002-0.003 inches. This would result in first and second portions 210, 220 with an outer diameter between 0.0195 and 0.0215 inches. By this structure, the first and second portions 210, 220 are capable of movement along the guidewire 100 with the guidewire 100 provided within the first and second portions 210, 220.

FIGS. 3-13 show an example of delivery and deployment of the embolic protection device 1 within the patient's blood vessel 110 in order to treat a stenosed region 111.

Figure 3:
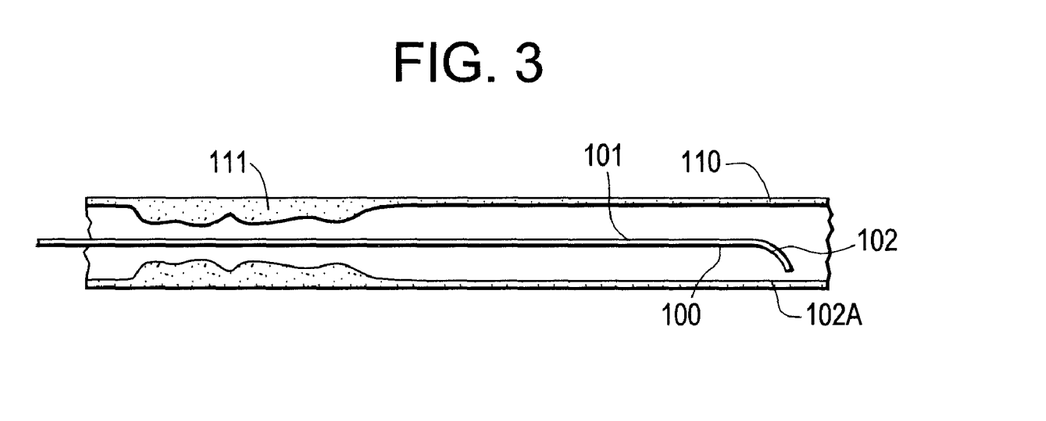
FIGS. 3-13 are schematic views illustrating delivery and deployment of the embolic protection device within a patient's blood vessel.

As shown in FIG. 3, a guidewire 100 is introduced into the blood vessel 110. The guidewire 100 includes a stiff elongated portion 101 and a floppy portion 102. The floppy portion 102 is the distal part of the guidewire 100 and typically makes up about 5-20 cm of the guidewire 100, although the invention is not limited in this respect. The floppy portion 102 includes a part with a stiffness that is less than the biasing force of the elastic elements 232, 234. Specifically, the floppy portion 102 can have a stiffness that gradually decreases from a stiffest portion adjacent to the elongated portion 101 to a floppiest (least stiff) portion at a distal end 102A of the guidewire 100. Accordingly, there is a point within the area of gradually decreasing stiffness of the floppy portion 102 where the stiffness of the guidewire 100 will be less than the biasing force of the elastic elements 232, 234.

The construction of the distal, floppy portion 102 varies among guidewire designs, but typically consists of a tapered core wire, made from either stainless steel or NITINOL surrounded by covering, which may be a coil or a polymer coating. The profile of the tapered core wire is typically design specific, but the covering (e.g., coil or polymer coating) typically has an outer diameter that is consistent along the length of the guidewire 100. The invention is not limited by the design of the guidewire.

Figure 4:
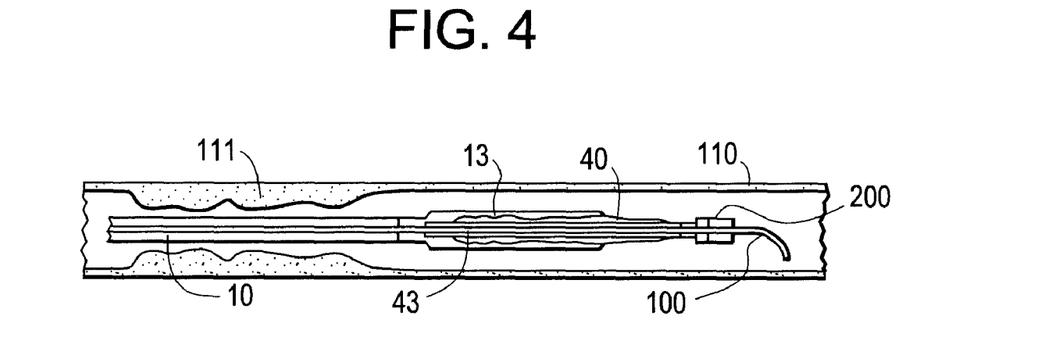

Thereafter, as shown in FIG. 4, the filter 40 is introduced into the blood vessel 110 along the guidewire 100 by a delivery catheter 10. The collapsed filter 40 may be provided within a pod 13 of the delivery catheter 10.

Figure 5:
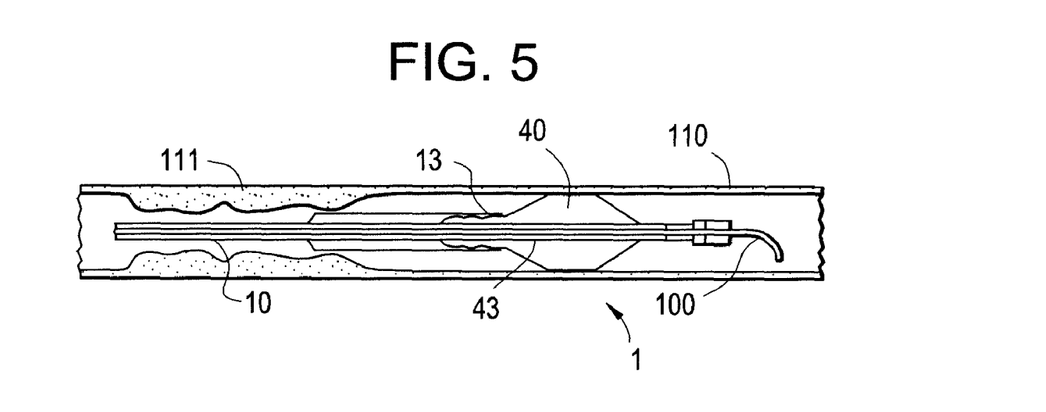
Figure 6:
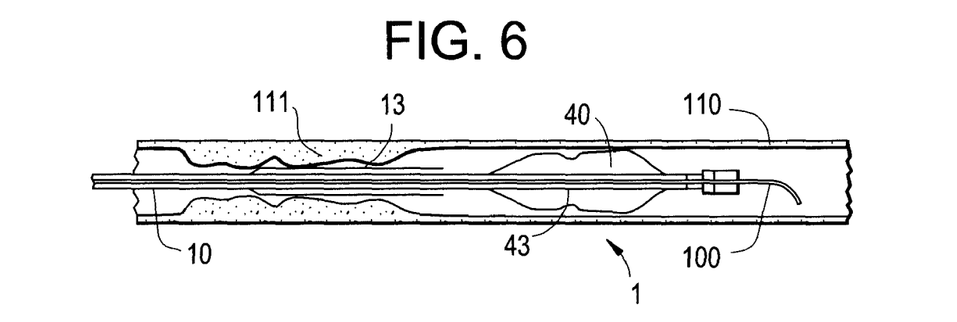
Figure 7:
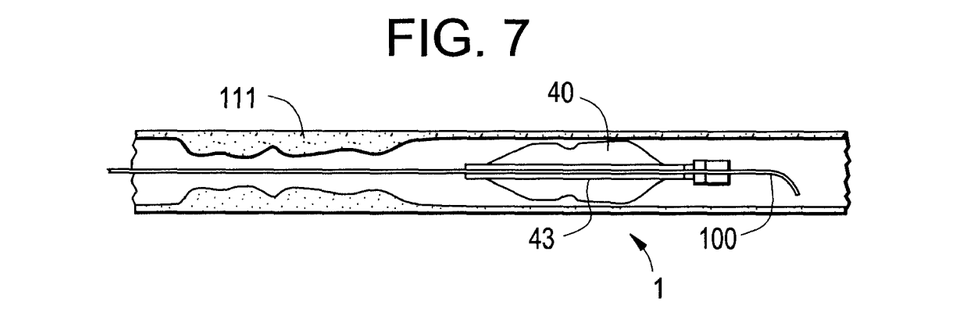

As shown in FIG. 5, when the filter 40 is advanced to a position distal to the stenosis 111, an inner stem of the delivery catheter 10 is retracted and the filter 40 expands within the blood vessel 110. At this time, the filter 40 is not fixed to the guidewire 100. Thereafter, as shown in FIGS. 6 and 7, the delivery catheter 10 is withdrawn from the blood vessel 110.

Figure 8:
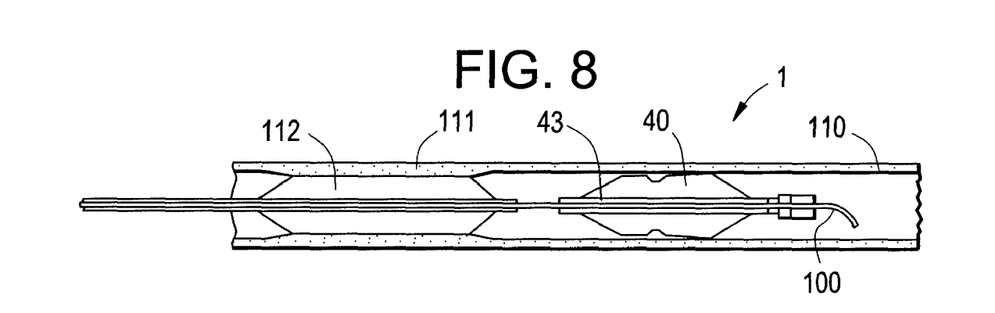
Figure 9:
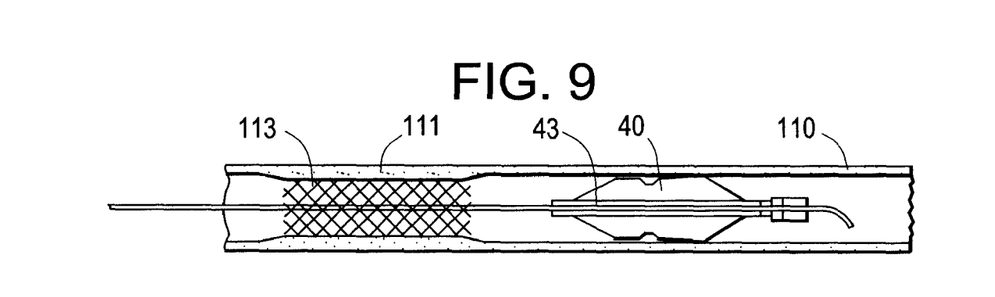
Figure 10:
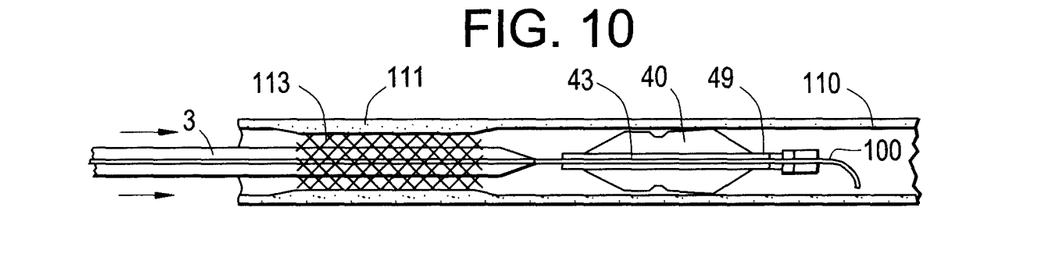

Then, a medical device is positioned within the stenosis 111. The medical device can be, for example, an atherectomy device, an angioplasty balloon 112 as shown in FIG. 8, or a stent 113 as shown in FIG. 9. However, the invention is not limited in this respect. Once the procedure on the stenosed region 111 of the blood vessel 110 is completed, as shown in FIG. 10, a retrieval catheter 3 is advanced toward the filter 40. Then, either the retrieval catheter 3 pushes the filter 40 toward the floppy portion 102 of the guidewire 100 or the guidewire 100 is retracted toward the filter 40.

Figure 11:
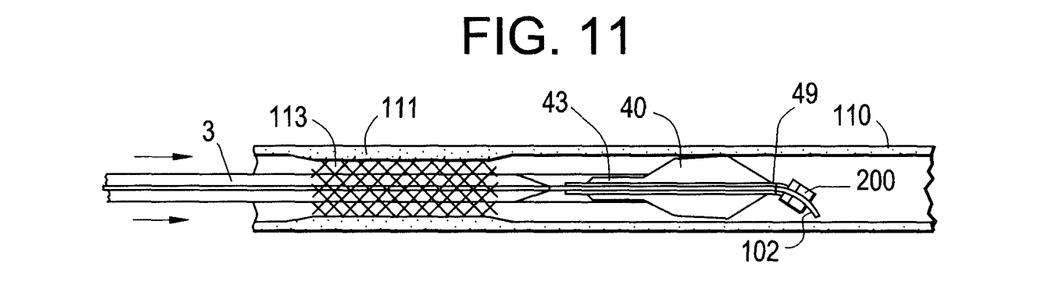

As shown in FIG. 11, when the lock 200 at the distal end of the filter 40 is positioned at the floppy portion 102 of the guidewire 100, a predetermined biasing force of the lock's elastic members 232, 234 overcomes the stiffness of the floppy portion 102 of the guidewire 100. This occurs at the position in the floppy portion 102 where the guidewire 102 no longer has enough stiffness to prevent the cylinders from folding over themselves.

Accordingly, the guidewire is biased so that the first and second portions 210, 220 are cinched, or no longer aligned. Therefore, the lock 200 cannot move in either transverse direction on the guidewire 100. Detailed schematics of the biasing of the lock 200 are shown in FIGS. 14A-15C.

At this time, the lock 200, and therefore the filter 40, is immovable to the floppy portion 102 of the guidewire 100. Because the filter 40 is held in place by the lock 200, the retrieval catheter 3 can be advanced over the filter 40, thereby collapsing the filter 40.

Figure 12:
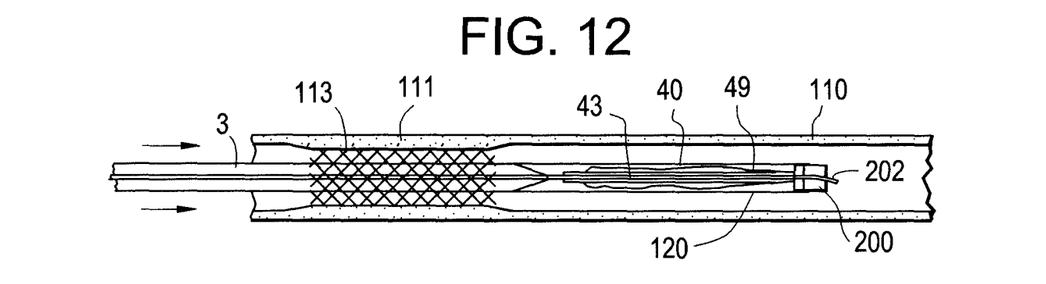
Figure 13:
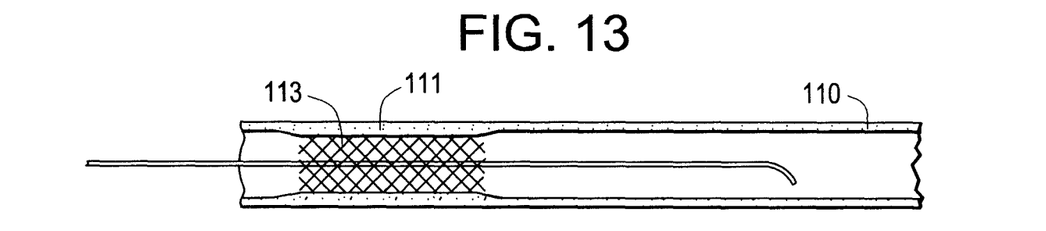

Moreover, as shown in FIG. 12, the retrieval catheter 3 can be further advanced over the lock 200 causing the first and second portions 210, 220 of the lock 200 to become aligned and, therefore, transversely moveable on the guidewire. Then, the filter 40 and the lock 200 (i.e., the embolic protection device 1) are released from the guidewire 100 and, as shown in FIG. 13, can be retracted from the blood vessel 110. Alternatively, once the filter 40 is collapsed, the embolic protection device 1, which is still immoveable to the guidewire 100, can be removed when the guidewire 100 is retracted.

Figure 14A:
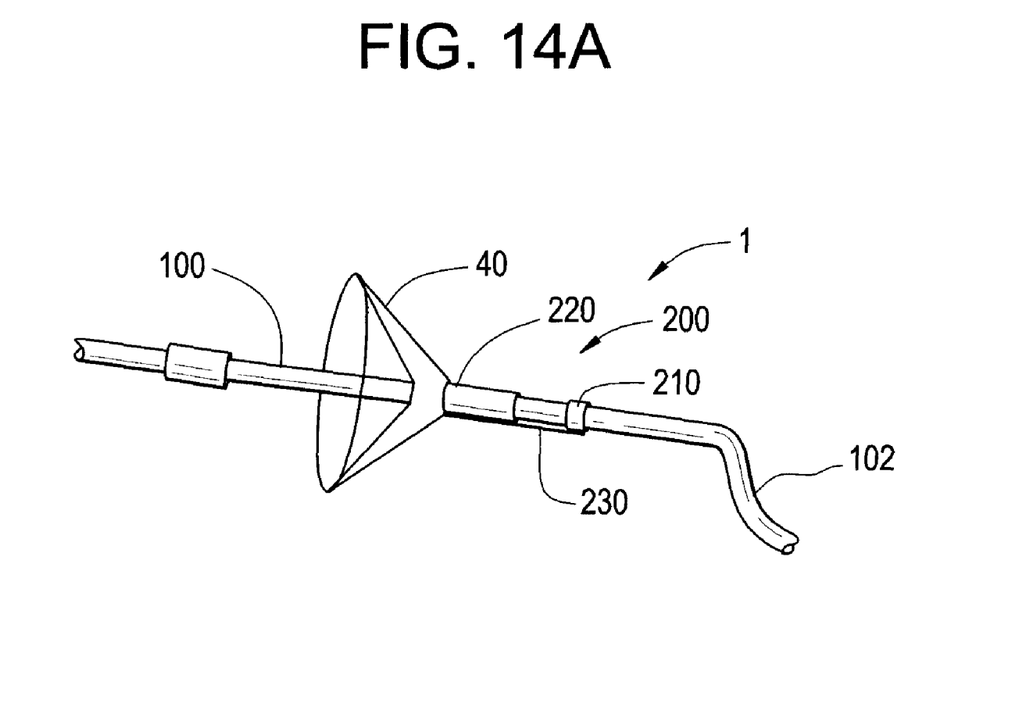
FIG. 14A shows the embolic protection device with the locking device in an unlocked, transversely moveable position on the guidewire.

FIG. 14A is a schematic view of the embolic protection device 1 in a first position, in which the first and second portions 210, 220 of the lock 200 and the biasing member 230 are aligned with respect to one another and with respect to the guidewire 100. At this position, the stiffness of the guidewire 100 is greater than the biasing force of the biasing member 230. Accordingly, the first and second portions 210, 220 are held in an aligned position by the guidewire 100 and are transversely moveable along the guidewire 100.

Figure 14B:
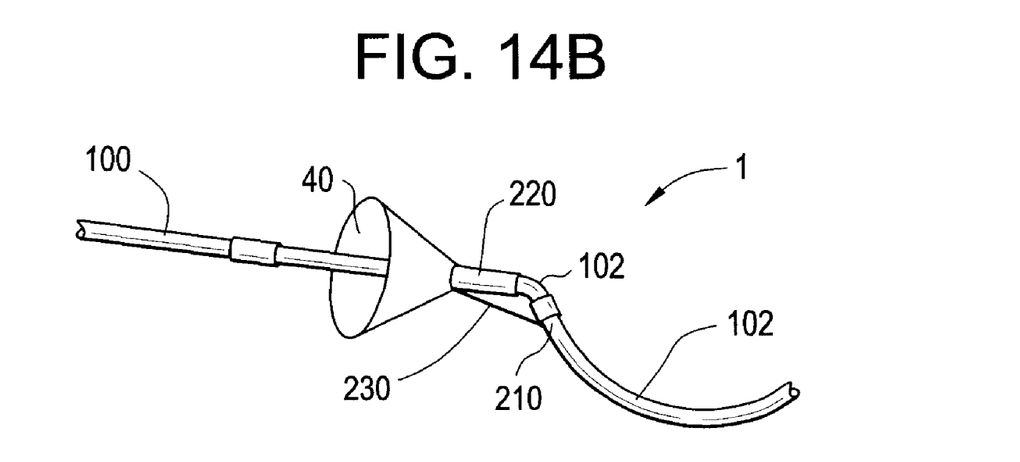
FIG. 14B shows the embolic protection device of the first exemplary embodiment locked to the guidewire.

FIG. 14B is a schematic view of the embolic protection device 1 in a second position, in which the first portion 210 of the lock 200 is oriented at an angle, and therefore no longer aligned, with respect to the second portion 220. At this second position, the predetermined biasing force of the elastic member 230 overcomes the stiffness of the floppy portion 102, causing the first portion 210 to be moved out of alignment with respect to the second portion 220. In this second position, the embolic protection device 1 is restricted from moving in both transverse directions on the guidewire 100. Thus, the embolic protection device 1 is locked to the guidewire 100.

Figure 15A:
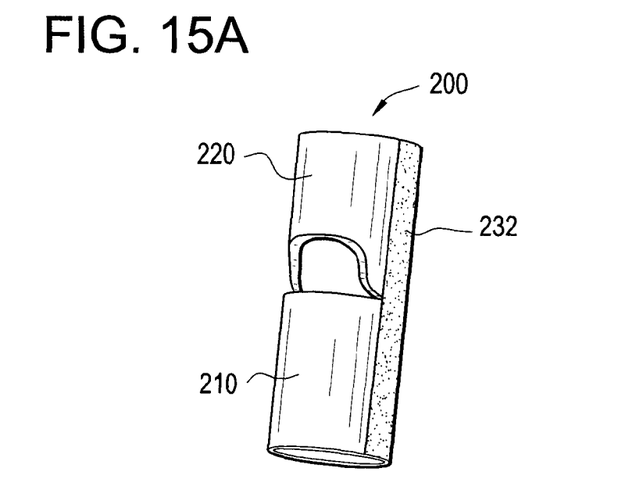
FIG. 15A shows the first exemplary embodiment of the lock at a first position.
Figure 15B:
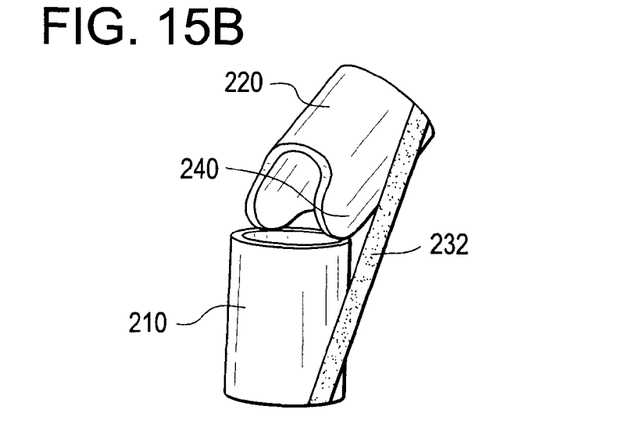
FIG. 15B shows the first exemplary embodiment of the lock at an intermediate position between the first position and a second position.
Figure 15C:
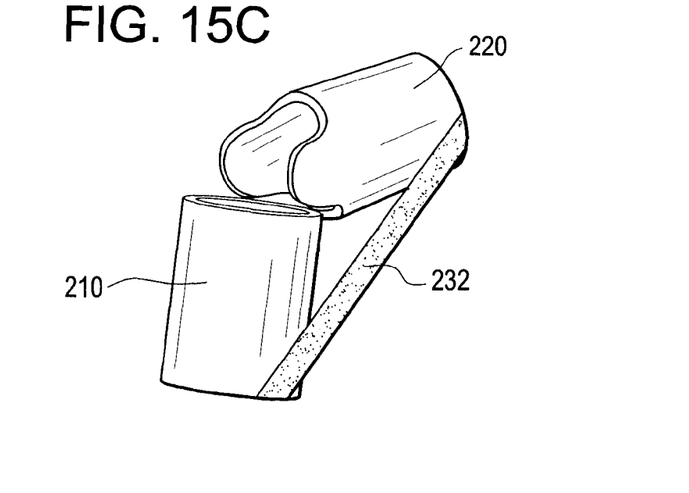
FIG. 15C shows the first exemplary embodiment of the lock in a second, locked position.

FIG. 15A shows the lock 200 in a transversely movable position, which exists when the stiffness of the guidewire 100 maintains alignment of the first and second portions 210, 220. FIG. 15B shows the lock 200 being biased toward the locked position, which exists when the predetermined biasing force of the elastic member 230 (i.e., elastic elements 232, 234) overcomes the stiffness of the floppy portion 102 of the guidewire 100. The first portion 210 abuts against the second portion 220 and rotates about the point contact 240 of the second portion 220 so that the first portion 210 is oriented at an angle with respect to the second portion 220. FIG. 15C shows the lock 200 at a final locked position, which exists when the elastic elements 232, 234 reach a neutral, unbiased state.

Figure 16:
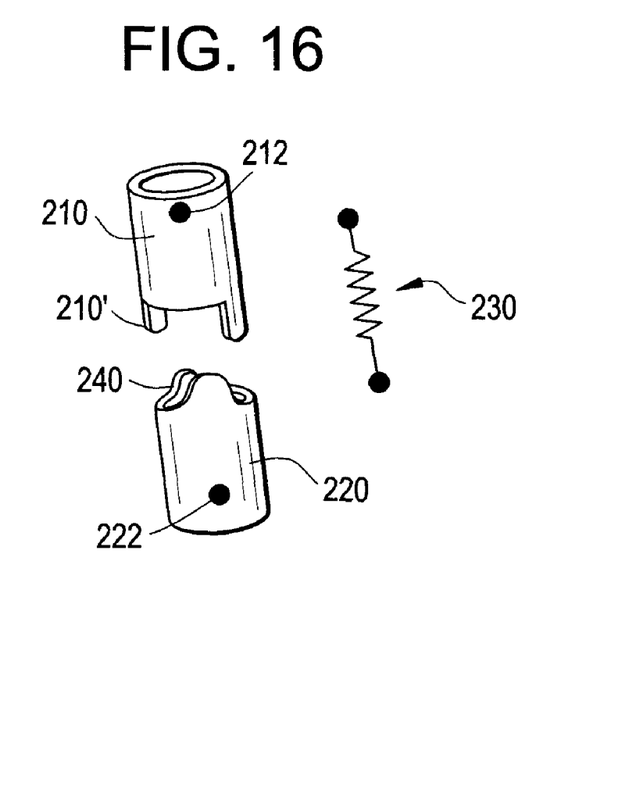
FIG. 16 shows the parts of a modification of the first exemplary embodiment.

FIG. 16 is a schematic of a modification of the first exemplary embodiment of the lock 200. The lock includes a first portion 210, a second portion 220, and a biasing member 230 (indicated by a spring shaped member). The biasing member 230 is connected between points at ends 212, 222 of the first portion 210 and second portion 220, respectively, and the second portion 220 includes the point contact 240. In this modification, the first modification includes two tabs 210' that are provided at positions that are 90 degrees with respect to the position of the biasing member 230. These tabs 210' allow the first portion 210 to provide a better contact with the floppy portion 102 of the guidewire 100.

Figure 17A:
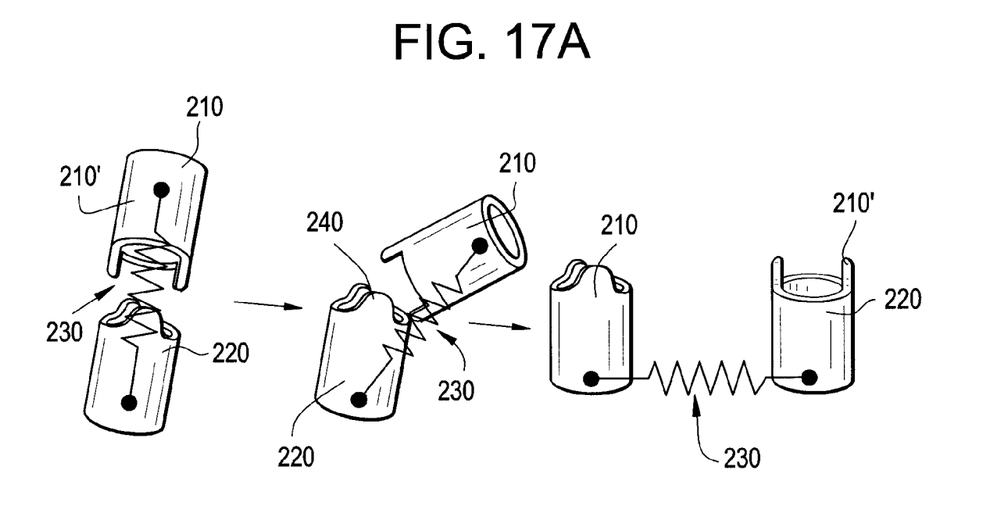
FIGS. 17A and 17B compare the movement of the first and second portions of the modification of the first exemplary embodiment if they were not provided on a guidewire with the movement of the first and second portions when they are provided on a guidewire.

FIG. 17A illustrates the biased movement of the first and second portions 210, 200 if they were not provided on a guidewire 100. That is, if the first and second portions 210, 220 were not provided on the guidewire 100, the biasing force of the elastic member 230 would bias the first portion 210 from an aligned position to a position where the first portion 210 and the second portion 220 are parallel to one another.

Figure 17B:
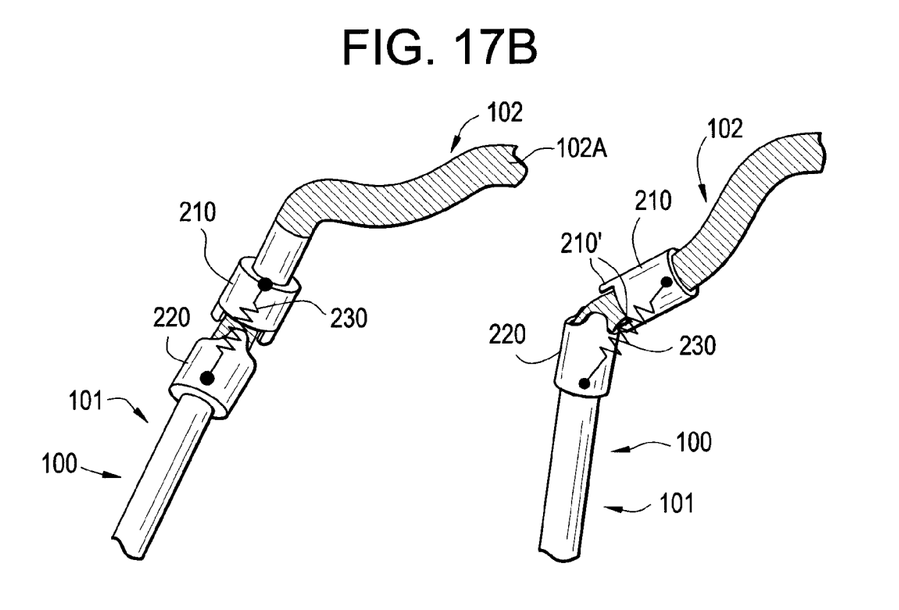

In contrast, FIG. 17B illustrates the biased movement of the first and second portions 210, 200 of the first embodiment when they are provided on a guidewire 100. Although the elastic member 230 partially overcomes the stiffness of the floppy portion 102 of the guidewire 100, the floppy portion 102 has some stiffness, which prevents the first portion 210 from moving to a position where the first portion 210 and the second portion 220 are next to one another. As shown in this figure, the lower tab 210' contacts the floppy portion 102 of the guidewire 102, providing a better locking force.

Figure 18:
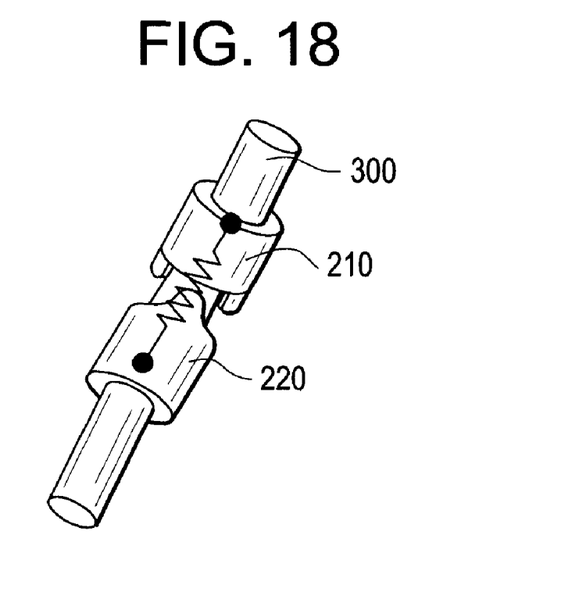
FIG. 18 shows the first and second portions of the modification of the first exemplary embodiment provided on a pin.

FIG. 18 shows the first and second portions 210, 220 provided on a pin, or stylet 300. It is expected that, when the embolic protection device 1 of first exemplary embodiment is packaged for sale, the pin 300 will be provided within the first and second portions 210, 220. Thereafter, before use of the filter 40 and lock 200, the guidewire 100 is provided within the filter 40 and lock 200. The guidewire 100 will push the pin 300 out from within the first and second portions 210, 220, and the filter 40 and lock 200 will be properly positioned on the guidewire 100 for insertion into the patient's body. It is also possible to use a tube in place of the pin, or a tube with an internal stop, that allows the guidewire to be inserted easily, and upon insertion, the guidewire will contact the stop and urge the tube out of the first and second portions, leaving the guidewire disposed within the portions as desired.

Figure 19A:
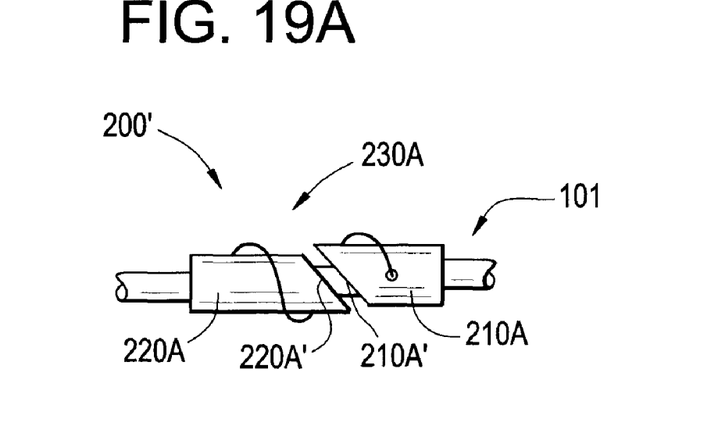
FIGS. 19A and 19B show a second exemplary embodiment of the lock.
Figure 19B:
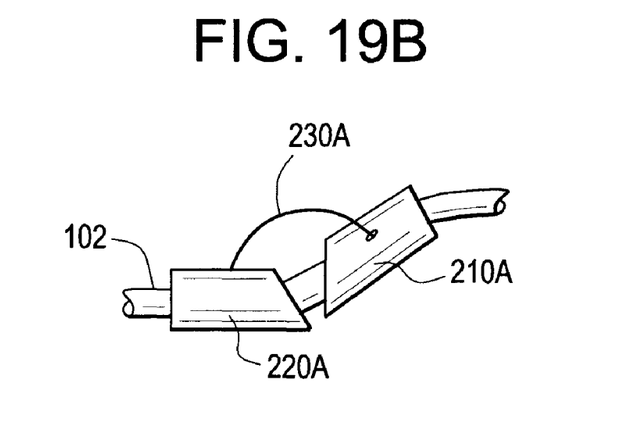

FIGS. 19A and 19B show a second exemplary embodiment of the lock 200' that can be used with the filter 40. In this exemplary embodiment, instead of using an elastic member 230 that is aligned with respect to the guidewire 100 in the first, aligned position, a helical elastic member 230A is connected between a first portion 210A and a second portion 220B. The first portion 210A includes a proximal end 210A' that is inclined at about 45 degrees, and the second portion includes a distal end 220A' that is inclined at about 45 degrees. The inclined proximal end 210A' of the first portion 210A is adjacent to the inclined distal end 220A' of the second portion 220A.

That is, as shown in FIG. 19A, when the first portion 210A, and second portion 220A are provided on the stiff portion 101 of the guidewire 100 (i.e., the first position), the inclined ends 210A', 220A' are arranged such that the first and second portions 210A, 220A form a substantially cylindrical shape. Moreover, as shown in FIG. 19B, when the first portion 210A, and second portion 220B are provided on the floppy portion 102 of the guidewire 100 (i.e., the second position), the biasing force of the elastic member 230A overcomes the stiffness of the floppy portion 102 of the guidewire 100. This causes the first portion 210A to rotate with respect to the second portion 220A.

The rotation of the first portion 210A causes the inclined ends 210A', 220A' to be moved to a position in which the first portion 210A and second portion 220A no longer form a substantially cylindrical shape. That is, as shown in FIG. 19B, the first portion 210A and second portion 220A are oriented at an angle with respect to one another (i.e., second position). One of ordinary skill will understand that the amount of rotation of the first portion 210A depends on the elasticity of the elastic member 230A, the stiffness of the floppy portion 102, and the positions where the elastic member 230A is attached to the first and second portions 210A, 220A.

Moreover, one or both of the first and second portions 210, 220 could include a structure that prevents the first portion 210A from rotating more than 180 degrees. This would prevent the first and second portions 210, 220 from rotating 360 degrees. That is, if the first portion 210A is allowed to rotate 360 degrees, the first and second portions 210, 220 would again form an aligned, substantially cylindrical shape and be transversely moveable, rather than locked in place.

Figure 20A:
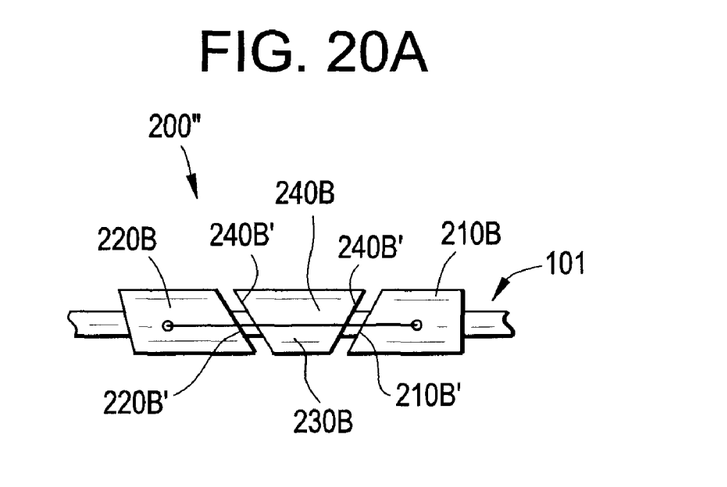
FIGS. 20A and 20B show a third exemplary embodiment of the lock.
Figure 20B:
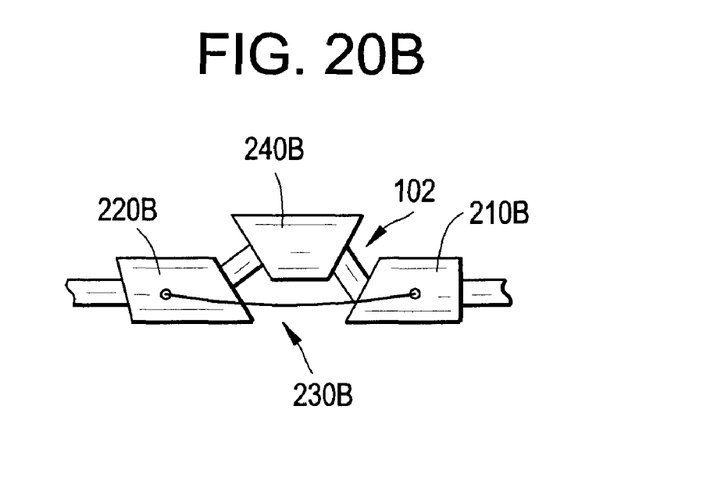

FIGS. 20A and 20B show a third exemplary embodiment of the lock 200". In this exemplary embodiment, an elastic member 230B, a first portion 210B, and a second portion 220B are aligned with respect to the guidewire 100 in a first, aligned position. However, unlike the first exemplary embodiment, in this exemplary embodiment, a third portion 240B is provided between the first portion 210A and the second portion 220B.

That is, as shown in FIG. 20A, when the first portion 210B, second portion 220B, and third portion 240B are provided on the stiff portion 101 of the guidewire 100 (i.e., the first position), inclined ends 210B', 220B', and 240B' of the portions 210B, 220B, 240B are arranged such that the portions 210B, 220B, 240B form a substantially cylindrical shape. Moreover, as shown in FIG. 20B, when the portions 210B, 220B, 240B are provided on the floppy portion 102 of the guidewire 100 (i.e., the second position), the biasing force of the elastic member 2301B overcomes the stiffness of the floppy portion 102 of the guidewire 100. This causes the third portion 240B to be laterally offset with respect to the other portions 2101B, 220B. Accordingly, the lock 200" is locked to the guidewire 100.

Figure 20C:
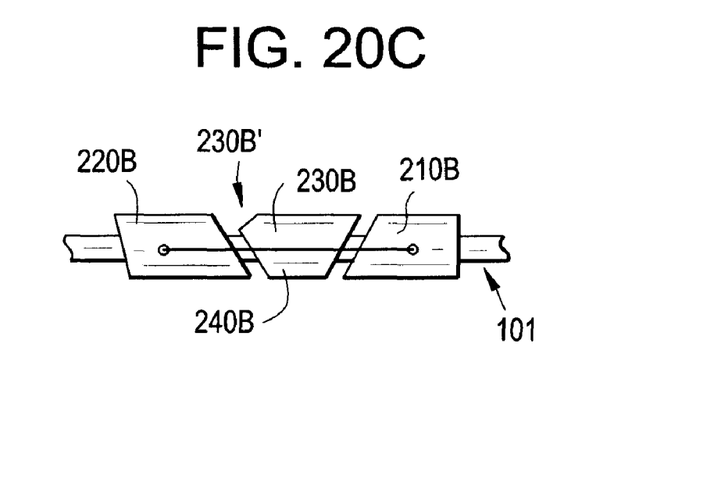
FIG. 20C shows a modification of the third exemplary embodiment.

Moreover, as shown in FIG. 20C, the third portion 240B can include an additional inclined portion 230B'. This inclined portion 230B' provides a surface that first contacts the retrieval catheter 3, when the retrieval catheter 3 is advanced over the filter 40 in order to re-align the portions 210B, 220B, 240B so that the filter 40 and lock 200″ can be withdraw from the blood vessel 110. Accordingly, the retrieval catheter 3 can easily push the portions 210B, 220B, and 240B back into alignment.

Figure 21:
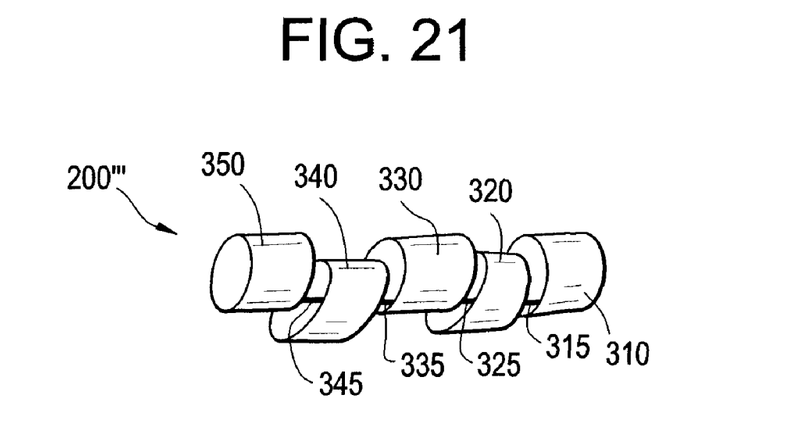
FIG. 21 shows a fourth exemplary embodiment of the lock.

Finally, FIG. 21 shows a third exemplary embodiment of the lock 200‴ in a non-aligned position. In this exemplary embodiment, the lock 200‴ includes several transversely moveable portions 310, 320, 330, 340, 350 that are attached to each other by connection portions 315, 325, 335, 345. The transversely moveable portions 310, 320, 330, 340, 350 and connection portions 315, 325, 335, 345 can be made of a shape memory material, such as NITINOL.

Accordingly, in the non-aligned position (i.e., second position), a shape-memory force of the shape-memory of the transversely moveable portions 310, 320, 330, 340, 350 and connections 315, 325, 335, 345 overcomes the stiffness of the floppy portion 102 of the guidewire 100. This causes the lock 200‴ to be locked in place. In contrast, in an aligned position (i.e., first position), the stiffness of the guidewire 100 overcomes the shape memory of the shape memory material and aligns the transversely moveable portions 310, 320, 330, 340, 350 in a substantially cylindrical shape. In this first position, the transversely moveable portions 310, 320, 330, 340, 350, and therefore, the filter 40, can move transversely along the guidewire 100.

Like the third exemplary embodiment, in this exemplary embodiment, the transversely moveable portions 310, 320, 330, 340, 350 can include inclined portions, which provide surfaces that first contact the retrieval catheter 3, when the retrieval catheter 3 is advanced over the filter 40 and lock 200‴. Accordingly, the retrieval catheter 3 can easily push the transversely moveable portions 310, 320, 330, 340, 350 back into alignment.

Figure 22:
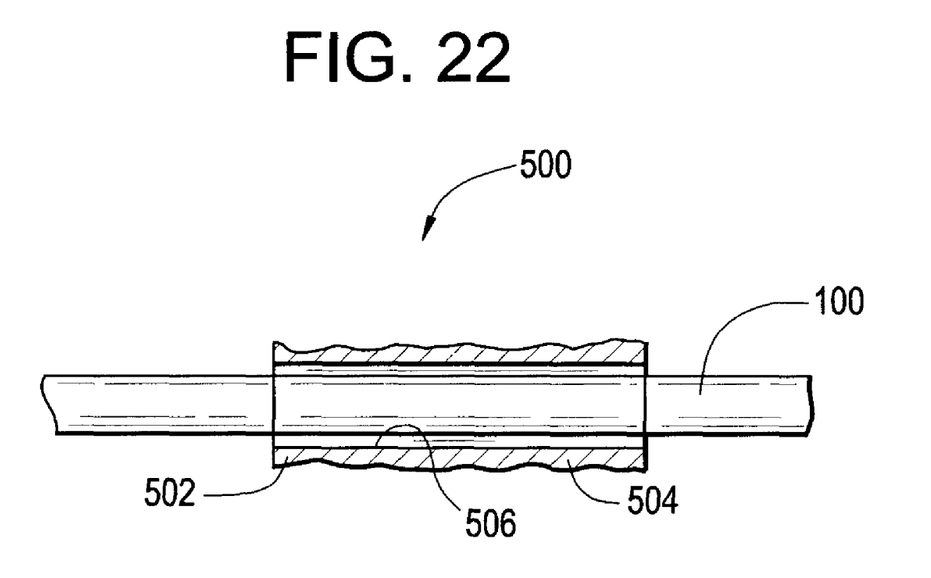
FIG. 22 shows a fifth exemplary embodiment of the lock in an unlocked configuration.

Referring now to FIG. 22, there is shown another embodiment of a lock in accordance with the present invention. In this embodiment, the lock comprises a tubular element 500 having a first end 502 and a second end, an inner lumen 506 and a wall thickness 504. The inner lumen 506 is sized and configured to be disposed on a guidewire 100, and the first end 502 is sized and configured to abut against an end of a filter device 600. As a result of the wall 504 geometry, dimensions, or the material properties, the tubular member is capable of undergoing strain in the axial direction.

Figure 23:
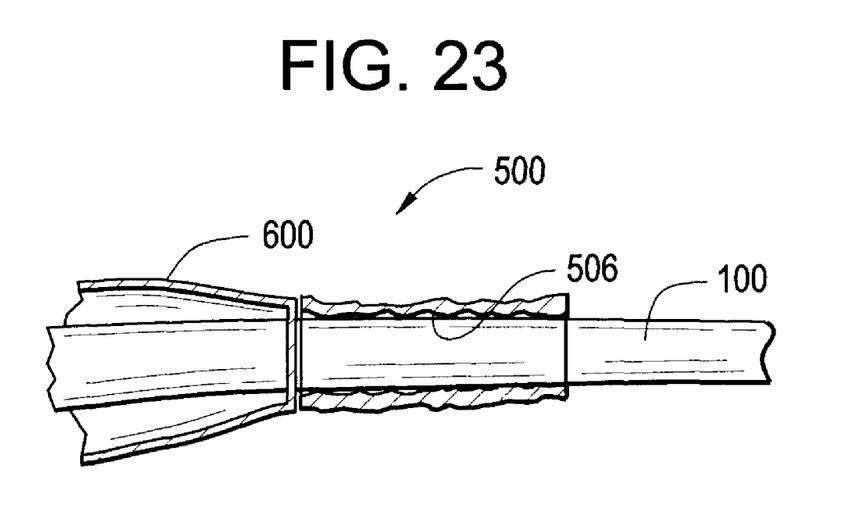
FIG. 23 shows a fifth exemplary embodiment of the lock in a locked configuration.

Referring now to FIG. 23, when the tubular member is strained in the axial direction, the average lumen diameter decreases. A reduction in average lumen diameter causes the tubular element 500 to hinder the movement of a guidewire 100 that it is disposed on, thereby locking it to the guidewire 100. Axial strain may be caused, for example, when a guidewire 100 frictionally engages the inner lumen 506 in one direction and when a filter device 600 applies an axial load to the proximal end in one direction.

It is contemplated that the tubular element 500 may be unlocked by passing a secondary catheter 800 over the tubular element 500. The secondary catheter 800 has an internal lumen sized and configured to contact the outer surface of the tubular element 500, and when it passes over the tubular element 500 it causes an axial strain in a direction opposite to that strain which caused the tubular element 500 to lock onto the guidewire 100. This reversed strain will unlock the tubular element 500.

In accordance with this embodiment, the tubular element 500 may be constructed of a metal, such as stainless steel, nitinol, CoCr, or any other suitable metal, or it may be constructed of a plastic, such as Pebax, polyurethane, TPE, or any other suitable plastic.

It is contemplated that the use of more rigid materials such as metals may require a tubular element 500 with a mesh-like construction. The mesh-like construction is intended to expand and contract in diameter when an axial load is applied to the tubular element 500. The mesh-like construction may be formed by braiding strands of wire, or by removing material from a solid tube, using fabrication methods such as laser-cutting, micro-machining, photo-etching, or other methods that are well known in the art.

In further accordance with this embodiment, when a mesh-like tubular element 500 is disposed on a guidewire 100, movement of the guidewire 100 in a distal direction will cause contact between the surface of the tubular element 500 lumen and the guidewire 100. This contact will result in a frictional load that tends to elongate the tubular element 500 in an axial direction. When a threshold limit of elongation is reached by the tubular element 500, the lumen diameter will reduce sufficiently to hinder movement of the guidewire 100 through the lumen of the tubular element 500.

In accordance with the present invention, it will be appreciated that a tubular element 500 made from a thin-walled elastomeric material, and a mesh-like tubular element 500 made from a more rigid material may be combined in order to form a tubular element 500 that hinders movement of a guidewire 100 in both transverse directions.

Figure 24:
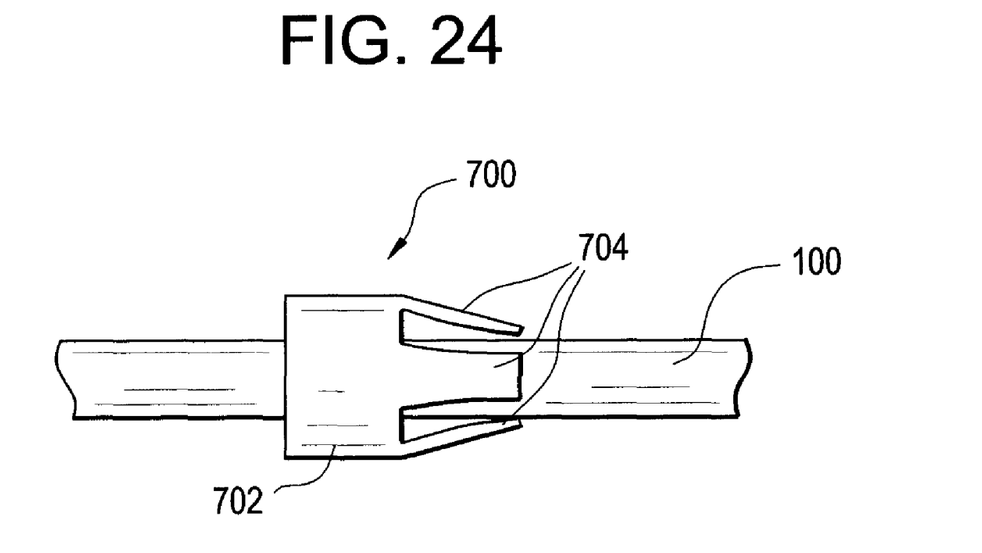
FIG. 24 shows a sixth exemplary embodiment of the lock disposed on a guidewire.

Referring now to FIG. 24, there is shown yet another embodiment of the lock in accordance with the present invention. In this embodiment, the lock comprises a collet 700 having a base and one or more teeth extending from the base in a generally axial direction. The teeth are shown to have a tapered construction, which provides the advantage of improved deliverability; however this is not necessary to the invention. The base includes a first end 706, capable of abutting against a filter device 600.

The collet teeth 704 can be deflected in a generally radial direction, and when disposed on a guidewire 100, deflecting them in the radially inward direction results in contact between the collet teeth 704 and the guidewire 100. When the guidewire 100 slides against the teeth in a direction counter to the direction of tooth extension from the base, the collet teeth 704 are urged radially inward and movement of the guidewire 100 is inhibited. This locks the collet 700 to the guidewire 100.

In further accordance with this embodiment, the collet teeth 704 may comprise surfaces that further prevent movement of the guidewire 100 when the collet 700 is engaged. For example, the collet surface may be roughened, gnarled, include ridges, or have any other structural elements that would result in a similar effect. Additionally, the collet teeth 704 may have surfaces formed from a material with a friction of coefficient that is higher than the collet base 702 material. For example, the collet base 702 may be formed from stainless steel or Nitinol, while the collet teeth 704 may include a low durometer polyurethane for its construction.

Figure 25:
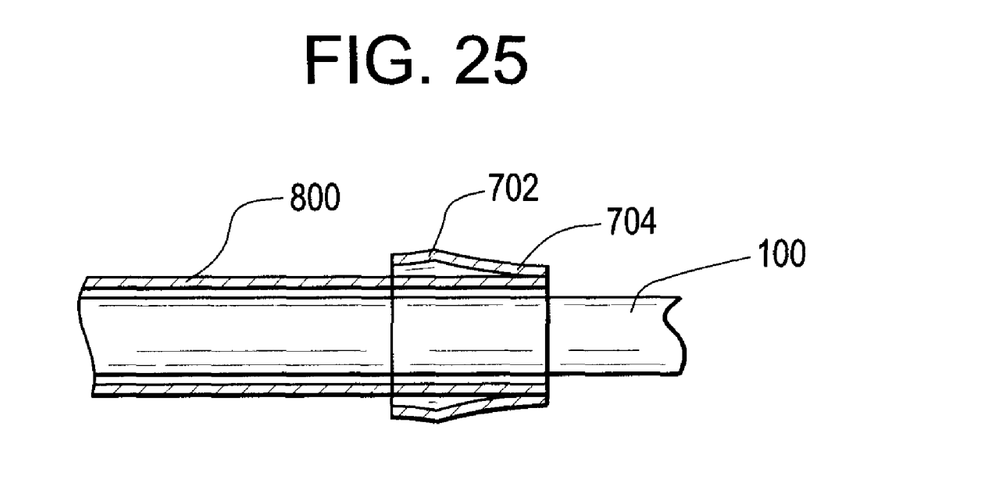
FIG. 25 shows a sixth exemplary embodiment of the lock in an unlocked configuration.

Referring now to FIG. 25, the collet 700 may be unlocked from the guidewire 100 by passing a secondary catheter 800 between the collet teeth 704 and the guidewire 100. The secondary catheter 800 is sized to slide within the collet 700, and forces the collet teeth 704 in a radially outward direction, thereby unlocking the collet 700.

It will be appreciated that the collet 700 may be deployed onto the guidewire 100 by delivering it over the guidewire 100 on a secondary catheter 800 to the deployment location. A tertiary catheter sized and configured to be delivered over the secondary catheter 800, and having a first end sized to abut the first end of the collet base 702 can then be advanced over the secondary catheter 800. The first end of the tertiary catheter may be pressed against the first end of the collet base 702 and the collet 700 is thereby removed from the secondary catheter 800, becoming disposed on the guidewire 100, as shown in FIG. 24.

The invention is not limited to the exemplary embodiments described above. That is, departures can be made from the exemplary embodiments without departing from the spirit and scope of the invention, which is only limited by the following claims.

What is claimed is:

1. A device for locking onto a guidewire, comprising:
   an element transversely movable along the guidewire, the element comprising a plurality of portions: and
   a biasing member connecting a first portion and a second portion of the transversely moveable element, the biasing member having a biasing force; wherein
   the first portion and another portion of the transversely moveable element are movable from a first position, where the first portion and the other portion are aligned with respect to one another, to a second position, where the first portion is not aligned with respect to the other portion, the device being locked to the guidewire in the second position;
   the guidewire comprises sections of varying stiffness, including a first section having a stiffness greater than the biasing force of the biasing member and a second section having a stiffness less than the biasing force of the biasing member, and
   the device moves from the first position to the second position when the device reaches the second section of the guidewire.

2. The device according to claim 1, wherein the other portion is the second portion, and the first and second portions are oriented at an angle at the second position.

3. The device according to claim 1, wherein at least one of the portions of the transversely moveable element is substantially cylindrically shaped.

4. The device according to claim 3, wherein each portion of the transversely moveable element is substantially cylindrically shaped.

5. The device according to claim 1, wherein the biasing member comprises an elastic member that biases the first and second portions of the transversely movable member.

6. The device according to claim 5, wherein the other portion is the second portion and the second portion is laterally offset with respect to the first portion at the second position.

7. The device according to claim 6, wherein the first portion comprises two opposing tabs, each tab provided at an end of the first portion that is adjacent to the second portion and at a position substantially 90 degrees with respect to the elastic element.

8. The device according to claim 5, wherein the elastic member comprises two elastic elements that are aligned with the guidewire in the first position, each elastic element being attached at a first end to the first portion of the transversely moveable element and at a second end to the second portion of the transversely moveable element.

9. The device according to claim 1, wherein the first and second portions of the transversely moveable element abut, and the first portion and/or the second portion have an end shaped to move the first and second portions from the first position to the second position.

10. The device according to claim 9, wherein the first portion and/or the second portion have an end having a shape that provides for limited contact between the first and second portions.

11. The device according to claim 10, wherein the first portion and/or the second portion have an end having a shape that provides for substantially point contact between the first and second portions.

12. The device according to claim 2, wherein the other portion is the second portion, and the biasing element comprises a helical elastic element that is connected between the first portion and the second portion.

13. The device according to claim 12, wherein the first portion comprises an inclined proximal end, and the second portion comprises an inclined distal end, wherein the inclined proximal end of the first portion is adjacent to the inclined distal end of the second portion.

14. The device according to claim 13, where the inclined portions are arranged such that the first and second portions form a substantially cylindrical shape at the first position.

15. The device according to claim 1, wherein the other portion is a third portion provided between the first and second portions, wherein the third portion is laterally offset with respect to the first and second portions at the second position.

16. The device according to claim 15, wherein the first portion comprises an inclined proximal end, the second portion comprises an inclined distal end, and the third portion comprises an inclined distal end and an inclined proximal end.

17. The device according to claim 16, wherein the inclined portions are arranged such that the first, second, and third portions form a substantially cylindrical shape at the first position.

18. The device according to claim 5, wherein the other portion is laterally offset with respect to the first portion at the second position.

19. An embolic protection device, comprising:
   the device for locking onto the guidewire according to claim 1; and
   a filter moveable on the guidewire, wherein the guidewire is adapted to be introduced into a vascular system of a patient.

20. The embolic protection device of claim 19, wherein the filter comprises:
   a collapsible filter body adapted for delivery through the vascular system of the patient, the filter body being moveable between a collapsed position, which is capable of movement through the vascular system, and an expanded position, which is capable of capturing embolic material while allowing blood to pass through the filter body;
   the filter body comprising an inlet end and an outlet end, the inlet end having inlet openings sized to allow the blood and the embolic material to enter the filter body, and the outlet end having a plurality of outlet openings sized to allow passage of the blood but to retain the embolic material within the filter body.

21. The device according to claim 19, wherein the other portion is the second portion, and the first and second portions are oriented at an angle at the second position.

22. The method according to claim 19, wherein the first portion is laterally offset with respect to the other portion at the second position.

23. The device according to claim 19, wherein at least one of the portions of the transversely moveable element is substantially cylindrically shaped.

24. The device according to claim 19, wherein the biasing member comprises an elastic member that biases the first and second portions of the transversely moveable element.

25. The embolic protection device of claim 19, wherein the device according to claim 1 in the second position is adapted to hold the filter in place so that a retrieval catheter can be advanced over the filter, thereby collapsing the filter.

26. The device of claim 1, wherein the second section of the guidewire is the distal end of the guidewire.

* * * * *